US005536892A

United States Patent [19]
Dolbier, Jr. et al.

[11] Patent Number: 5,536,892
[45] Date of Patent: Jul. 16, 1996

[54] PROCESSES FOR THE PREPARATION OF OCTAFLUORO-[2,2]PARACYCLOPHANE

[75] Inventors: William R. Dolbier, Jr.; Xiao X. Rong, both of Gainesville, Fla.

[73] Assignee: Specialty Coating Systems, Inc., Indianapolis, Ind.

[21] Appl. No.: 544,831

[22] Filed: Oct. 18, 1995

[51] Int. Cl.$^6$ .................................................. C07C 25/13
[52] U.S. Cl. .......................... 570/144; 570/143; 570/127
[58] Field of Search ...................................... 570/144, 143, 570/129, 127

[56] References Cited

U.S. PATENT DOCUMENTS

| | | |
|---|---|---|
| 3,268,599 | 8/1966 | Chow . |
| 3,274,267 | 9/1966 | Chow . |
| 3,280,202 | 10/1966 | Gilch . |
| 3,297,591 | 1/1967 | Chow . |
| 3,332,891 | 7/1967 | Chow et al. . |
| 3,405,117 | 10/1968 | Yeh . |
| 4,734,533 | 3/1988 | Ungarelli .................... 570/201 |
| 4,783,561 | 11/1988 | Prgaglia ..................... 570/184 |
| 4,795,838 | 1/1989 | Bornengo .................... 570/184 |
| 4,816,608 | 3/1989 | Bornengo .................... 570/184 |
| 4,846,998 | 7/1989 | Pohl .......................... 570/184 |
| 4,853,488 | 8/1989 | Ungarelli .................... 570/184 |
| 4,886,923 | 12/1989 | Ungarelli .................... 570/210 |
| 5,110,903 | 5/1992 | Lee .......................... 570/190 |
| 5,210,341 | 5/1993 | Dolbier, Jr. et al. . |
| 5,268,202 | 12/1993 | You et al. . |
| 5,302,767 | 4/1994 | Galley ....................... 570/184 |

OTHER PUBLICATIONS

Chow, S. et al., Journal of Applied Polymer Science, vol. 13, pp. 2352–2332 (1969).

*Primary Examiner*—Alan Siegel
*Attorney, Agent, or Firm*—Salter & Michaelson

[57] ABSTRACT

A process for the preparation of octafluoro-[2,2]paracyclophane includes contacting a reactant selected from the group consisting of 1,4-bis (bromodifluoromethyl)benzene (dibromide), 1,4-bis (chlorodifluoromethyl)benzene (dichloride), and 1,4-bis (iododifluoromethyl)benzene (diiodide) with trimethylsilyltributyltin (TMSTBT) (a reducing agent) and fluoride ions in a refluxing solution of hexamethylphosphoramide (HMPA) or dimethylsulfoxide (DMSO) in tetrahydrofuran (THF) at conditions effective to promote a reaction product comprising octafluoro-[2,2]paracyclophane.

12 Claims, No Drawings

PROCESSES FOR THE PREPARATION OF OCTAFLUORO-[2,2]PARACYCLOPHANE

BACKGROUND AND SUMMARY OF THE INVENTION

The instant invention relates generally to processes for the preparation of parylene dimers, and more particularly to processes for the preparation of octafluoro-[2,2]paracyclophane, otherwise known as AF4.

Parylene is a generic term used to describe a class of poly-p-xylylenes which are derived from a dimer having the structure:

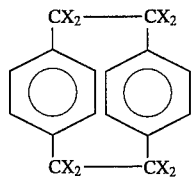

wherein X is typically a hydrogen, or a halogen. The most commonly used forms of parylene dimers include the following:

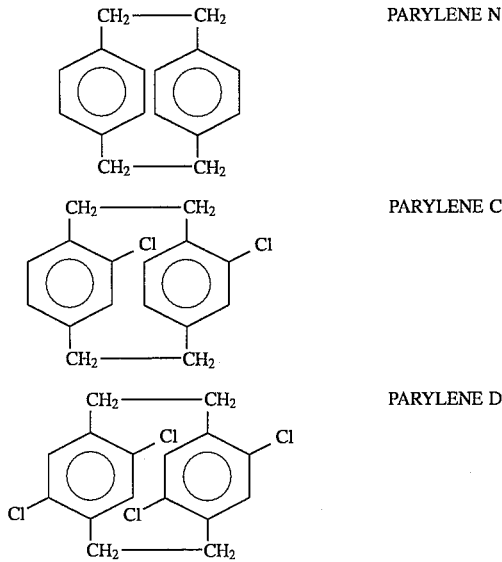

Parylene coatings are obtained from parylene dimers by means of a well-known vapor deposition process in which the dimer is vaporized, pyrolized, i.e. cleaved into a monomer vapor for, and fed to a vacuum chamber wherein the monomer molecules polymerize, and deposit onto a substrate disposed within the vacuum chamber.

Due to their ability to provide thin films and conform to substrates of varied geometric shapes, parylene materials are ideally suited for use as a conformal coating in a wide variety of fields, such as for example, in the electronics, automotive, and medical industries.

Octafluoro-[2,2]paracyclophane (AF4) is a fluorine substituted version of the above-noted dimers and has the structure:

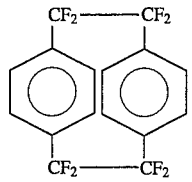

It is known that parylene coatings (Parylene $AF_4$) which are derived from the $AF_4$ dimer by the vapor deposition process have a very high melting temperature (about 540° C.), and a low dielectric constant (about 2.3). These characteristics make Parylene $AF_4$ ideally suited for many high temperature applications, including electronic applications, and potentially as an inter-layer dielectric material for the production of semiconductor chips. However, up to the present time, AF4, which is used as the dimer starting material for depositing Parylene F coatings, has been commercially unavailable due to high costs of production.

One known method of producing AF4 is described in U.S. Pat. No. 5,210,341 wherein the process of preparing AF4 utilizes a low temperature in conjunction with a reduced form of titanium in order to produce dimerization of dihalide monomers. One aspect of the '341 patent provides a process for preparing octafluoro-[2,2]paracyclophane, which comprises contacting a dihalo-tetrafluoro-p-xylylene with an effective amount of a reducing agent comprising a reduced form of titanium and an organic solvent at conditions effective to promote the formation of a reaction product comprising octafluoro-[2,2]paracyclophane.

While the process described in the '341 patent is effective for its intended purpose, it has been found that the process is still too expensive for commercial realization due to low yields, that there are some impurities in the AF4 dimer, and furthermore that it would be difficult to adapt to a large scale commercial production.

The instant invention provides improved processes for the preparation of octafluoro-[2,2]paracyclophane which involve contacting a reactant comprising 1,4-bis-(bromodifluoromethyl)benzene with a reducing agent comprising trimethylsilyltributyltin (TMSTBT), and fluoride ions in a refluxing solution of hexamethylphosphoramide (HMPA) or dimethylsulfoxide (DMSO) in tetrahydrofuran (THF) at conditions effective to promote the formation of a reaction product comprising octafluoro-[2,2]paracyclophane.

The dibromide reactant in the present invention is the reactant which is most efficiently converted to AF4. Alternatively, the analogous dichloride [1,4-bis(chlorodifluoromethyl)benzene], or diiodide [1,4-bis(iododifluoromethyl)benzene] may be used. However, the obtained yield of AF4 appears to be lower when using them in place of the dibromide.

In one preferred aspect of the invention, anhydrous tetrahydrofuran (THF), hexamethylphosphoramide (HMPA), and anhydrous cesium fluoride (CsF) are added under a nitrogen atmosphere to a flask provided with a mechanical stirrer. After initial warming and stirring, a quantity of trimethylsilyltributyltin (TMSTBT) is added to the mixture. After further stirring a predetermined quantity of 1,4-bis-(bromodifluoromethyl)benzene (otherwise referred to as dibromide) is added to the mixture. Over a period of up to 24 hours, additional quantities of CsF, TMSTBT, and dibromide are added to the mixture. After all of the dibromide is consumed by the formation reaction, the THF is removed by distillation, and evaporation, and then various other filtering, distillation, evaporation, and washing steps are conducted to yield a crystalline form of AF4 (8–14% yield).

In another preferred aspect of the invention, the HMPA in the above process is replaced by dimethylsulfoxide (DMSO). The later steps are substantially as described above, yielding a crystalline form of AF4. However, the yield is somewhat higher with the DMSO process (up to 40% yield).

Accordingly, among the objects of the instant invention are: the provision of improved processes for the preparation of octafluoro-[2,2]paracyclophane; and more specifically, the provision of improved processes for the preparation of octafluoro-[2,2]paracyclophane which involves contacting a reactant selected from the group consisting of 1,4-bis(bromodifluoromethyl)benzene, 1,4-bis(chlorodifluoromethyl)benzene, and 1,4-bis (iododifluoromethyl)benzene with a reducing agent comprising trimethylsilyltributyltin (TMSTBT), and fluoride ions in a refluxing solution of hexamethylphosphoramide (HMPA) or dimethylsulfoxide (DMSO) in tetrahydrofuran (THF) at conditions effective to promote the formation of a reaction product comprising octafluoro-[2,2]paracyclophane.

Other objects, features and advantages of the invention shall become apparent as the detailed description thereof proceeds.

DESCRIPTION OF THE PREFERRED EMBODIMENT

The instant processes for the preparation of octafluoro-[2,2]paracyclophane (AF4) comprise contacting 1,4-bis-(bromodifluoromethyl)benzene (otherwise referred to as dibromide) with a reducing agent and fluoride ions in a refluxing solution.

The dibromide reactant in the present invention is the reactant which is most efficiently converted to AF4. Alternatively, the analogous dichloride [1,4-bis(chlorodifluoromethyl)benzene], or diiodide [1,4-bis(iododifluoromethyl)benzene] may be used. However, the obtained yield of AF4 appears to be lower when using them in place of the dibromide.

The reducing agent of the present invention preferably comprises trimethylsilyltributyltin (TMSTBT). Alternatively, tributyltin lithium, bis-tributyltin, and hexamethyldisilane have also been found to be effective reducing agents. However, the obtained yield of AF4 appears to be quite lower when using these alternate reducing agents.

The fluoride ions are preferably provided by anhydrous cesium fluoride (CsF) mixed into the refluxing solution. Potassium fluoride (KF) is a suitable substitute for a source of fluoride ions. However, it has been found that the use of KF results in diminished yields over CsF.

The refluxing solution preferably comprises a mixture of either hexamethylphosphoramide (HMPA) or dimethylsulfoxide (DMSO) in an organic solvent, such as tetrahydrofuran. Dimethylformamide (DMF) and 2,4-dimethylimidazolidin-3-one are also effective replacements for the HMPA or DMSO, although their use results in diminished yields.

Other organic solvents are also suitable including diethyl ether, 1,4-dioxane, 1,2-dimethoxyethane, and 1,2-diethoxyethane.

Each of the compounds referred to above is well known in the chemical arts and is commercially available from a wide variety of sources. Accordingly, further detailed description of the compounds and their chemical characteristics is not believed to be necessary.

In the process of the present invention, the reactant is contacted with the TMSTBT and fluoride ions in a refluxing solution at conditions effective to promote the formation of a reaction product comprising octafluoro-[2,2]paracyclophane (AF4). Preferably, the fluoride ions, reactant and TMSTBT are added to the refluxing solution gradually, preferably in batches, at intervals of several hours. The term "gradually" is used herein to mean over a period of about 24 hours.

Typically the reducing agent (TMSTBT), CsF, and reactant are added to the mixture in generally equal molar quantities. It has been found that an excess of reducing agent is not necessary to promote the full reaction to completion.

The conditions effective for promoting the formation of AF4 include a temperature of between about 50° C. and 100° C. Preferably, the reaction is conducted under refluxing conditions. Thus, the temperature employed will preferably correspond to the boiling point of the particular organic solvent used in the refluxing solution. In the instant method, the preferred reaction temperature is about 78° C., which is the refluxing temperature of THF. The pressure utilized during the reaction is not critical to the invention, and can be subatmospheric, atmospheric, or superatmospheric. Typical pressures will range from about 0.1 atmospheres, to about 10 atmospheres. However, it is preferred that the reaction be performed in an inert atmosphere, such as, for example, under nitrogen, helium, or argon.

The recovery of AF4 from the reaction solution, either HMPA or DMSO, involves removal of the THF by distillation, filtering off the precipitate, and removing the remaining THF by rotary evaporation. The residual liquid is then distilled under vacuum.

With regard to the HMPA method, the distillate with a boiling point above 95° C. (0.5 mm Hg) is collected and four times this volume of chloroform added. The mixture is then washed with 50% sulfuric acid, aqueous solution, and finally brine. The organic layer is then dried over anhydrous $MgSO_4$, the solvent removed by rotary evaporation, 100 ml hexane added to the residue, and the solution placed in the refrigerator for about 12 hours to yield crystalline AF4, i.e. the mixture is chilled at a temperature of about 0°–10° C., for about 12 hours.

With regard to the DMSO method, the distillate having a boiling point above 70° C. (0.5 mm Hg) is collected and placed in the refrigerator for 12 hours, i.e. chilled at 0°–10° C. for 12 hours, to yield crystalline AF4. The crude product is then recrystallized from chloroform-hexane (10:1) (12 hours at 0°–10° C.) to yield pure AF4.

The AF4 dimer produced by these processes is particularly suitable for use in the production of Parylene F thin films, and can be deposited in a conventional manner according to well known CVD deposition techniques.

The following examples are provided for illustrative purposes and are not intended to limit the scope of the claims which follow.

EXAMPLE 1

Dibromide/HMPA Method

Ten (10) liters of anhydrous tetrahydrofuran (THF), one (1) liter of hexamethylphosphoramide (HMPA), and 27.2 g (0.18 mol) of anhydrous cesium fluoride (CsF) were introduced under a nitrogen atmosphere into a dried twelve (12) liter flask equipped with a mechanical stirrer, condenser, addition funnels, and a nitrogen inlet. The mixture was warmed to 70° C. and stirred for 0.5 hour. 52.5 g (0.14 mol) of trimethylsilyltributyltin (TMSTBT) were then added to the mixture, and the mixture was stirred for another 0.5 hour at a temperature below 70° C. The temperature was allowed to rise to 78° C. (refluxing THF), and then 55 g (0.16 mol) of 1,4-bis(bromodifluoromethyl) benzene (otherwise referred to as dibromide) were added all at once to the flask by means of a syringe inserted through a rubber septum. Under reflux and protected by the nitrogen atmosphere, the mixture was stirred for 12 hours, after which additional quantities of CsF (27.2 g,0.18 mol), TMSTBT (57.5 g, 0.16 mol), and dibromide (55 g, 0.16 mol) were added through individual addition funnels at a rate of one (1) drop per 10 seconds. After another 6 hours of stirring, third portions of CsF (27.2 g, 0.18 mol), TMSTBT (52.5 g, 0.14 mol), and dibromide (55 g, 0.16 mol) were similarly added to the mixture. A final portion of TMSTBT (37 g, 0.11 mol) was added after yet another 5 hours of stirring. Analysis of the mixture by $^{19}$FNMR after another 5 hours of stirring indicated that all of the dibromide had been consumed.

Nine (9) liters of THF were then removed by distillation at atmospheric pressure. The resulting mixture was then cooled to room temperature and let stand for 12 hours. Then, the precipitate was filtered off, and the remaining THF was removed by rotary evaporation. The residual liquid was then distilled under reduced pressure. The distillate with boiling point above 95° C. (0.5 mm Hg) was collected, and measured, and then four times this measured volume of chloroform was added to the mixture. The mixture was then washed with 50% sulfuric acid, aqueous solution, and finally brine. The organic layer was dried over anhydrous $MgSO_4$, and the solvent removed by rotary evaporation. 100 Ml of hexane was added to the residue, and the solution put in the refrigerator overnight (chilled at 0°–10° C. for about 12 hours) to yield 8–14 g of crystalline AF4 (10–16% yield).

EXAMPLE 2

Dibromide/DMSO Method

Eight (8) liters of anhydrous tetrahydrofuran (THF), two (2) liters of anhydrous dimethylsulfoxide (DMSO), and 55.3 g (0.36 mol) of anhydrous cesium fluoride (CsF) were added under a nitrogen atmosphere to a dried twelve (12) liter flask equipped with a mechanical stirrer, a condenser and a nitrogen inlet. The temperature of the mixture was allowed to rise to 70° C., and it was stirred for 0.5 hour. To this mixture was added 105.5 g (0.28 mol) of trimethylsilyltributyltin (TMSTBT), and the mixture stirred for 0.5 hour at 70° C. The temperature was then allowed to rise to 78° C. Under reflux and protected by the nitrogen atmosphere, 100 g (0.32 mol) of 1,4-bis(bromodifluoromethyl) benzene (otherwise referred to as dibromide) was added all at once to the mixture by means of a syringe inserted through a rubber septum. The mixture was then stirred for 12 hours, and then an additional 57.5 g (0.16 mol) of TMSTBT was added to the mixture, with a final portion of TMSTBT (52.5 g, 0.14 mol) being added after 6 more hours. Upon stirring for an additional 10 hours, it was determined by $^{19}$FNMR that all of the dibromide had been consumed.

Seven (7) liters of the THF were then removed by distillation at atmospheric pressure. The resulting mixture was then cooled to room temperature and let stand for 12 hours, after which the precipitate: was filtered off and the remaining THF was removed by rotary evaporation. The residual liquid was distilled under vacuum, with the distillate boiling above 70° C. (0.5 mm Hg) being collected and placed in a refrigerator for 12 hours (chilled at 0°–10° C. for about 12 hours), yielding 25 g of crystalline AF4. The crude product was recrystallized from chloroform-hexane (10:1) (chilled at 0°–10° C. for 12 hours in the refrigerator) to yield 22.7 g of pure AF4 (yield 40%).

It is to be noted that the use of pure THF, or substituting DMF or 2,4-dimethylimidazolidin-3-one for the HMPA or DMSO leads to product being formed in diminished yields. Further, the use of tributyltin lithium, bistributyltin or hexamethyldisilane as the reducing agent also leads to diminished yields of the product. Still further, substitution of potassium fluoride (KF) for cesium fluoride (CsF) also leads to a reduced yield of product.

It can therefore be seen that the instant invention provides unique and novel processes for the preparation of octafluoro-[2,2]paracyclophane. In particular, the instant processes have the advantage that they are simpler, cheaper, and safer than the prior art processes, and unlike the earlier titanium based technology, the TMSTBT technology has already been demonstrated to be scalable up to 100 g quantities of AF4 per run with little doubt that kilogram runs will be possible.

While there is described herein certain specific structure embodying the invention, it will be manifest to those skilled in the art that various modifications may be made without departing from the spirit and scope of the underlying inventive concept and that the same is not limited to the particular forms herein described except insofar as indicated by the scope of the appended claims.

What is claimed is:

1. A process for the preparation of octafluoro-[2,2]paracyclophane which comprises contacting a reactant selected from the group consisting of 1,4-bis (bromodifluoromethyl)benzene 1,4-bis(chlorodifluoromethyl)benzene and 1,4-bis(iododifluoromethyl)benzene with a reducing agent and fluoride ions at effective conditions to promote the formation of a reaction product comprising octafluoro-[2,2]paracyclophane.

2. The process of claim 1 wherein the effective conditions include an inert atmosphere.

3. The process of claim 1 wherein said reducing agent comprises trimethylsilyltributyltin.

4. The process of claim 3 wherein said effective conditions include contacting 1,4-bis(bromodifluoromethyl) benzene with trimethylsilyltributyltin and fluoride ions in a refluxing solution under reflux conditions.

5. The process of claim 4 wherein said refluxing solution comprises hexamethylphosphoramide in an organic solvent.

6. The process of claim 5 wherein said organic solvent comprises tetrahydrofuran.

7. The process of claim 6 wherein said refluxing conditions include a temperature of about 78° C.

8. The process of claim 4 wherein said refluxing solution comprises dimethylsulfoxide in an organic solvent.

9. The process of claim 8 wherein said organic solvent comprises tetrahydrofuran.

10. The process of claim 9 wherein said refluxing conditions include a temperature of about 78° C.

11. The process of claim 1 further comprising the step of recovering at least a portion of the octafluoro-[2,2]paracyclophane from the reaction product.

12. The process of claim 4 further comprising the step of recovering at least a portion of the octafluoro-[2,2]paracyclophane from the reaction product.

* * * * *